United States Patent [19]

Meyer

[11] 4,237,454

[45] Dec. 2, 1980

[54] SYSTEM FOR MONITORING BEARINGS AND OTHER ROTATING EQUIPMENT

[75] Inventor: Leslie D. Meyer, Schenectady, N.Y.

[73] Assignee: General Electric Company, Schenectady, N.Y.

[21] Appl. No.: 7,573

[22] Filed: Jan. 29, 1979

[51] Int. Cl.³ ............... G01H 13/00; G08B 21/00
[52] U.S. Cl. .................... 340/682; 73/593; 73/DIG. 4; 310/323; 340/539; 340/683
[58] Field of Search .......... 340/682, 683, 539, 58; 73/593, 659, DIG. 4; 325/185; 310/323

[56] References Cited

U.S. PATENT DOCUMENTS

| | | | |
|---|---|---|---|
| 2,875,353 | 2/1959 | Cavaliere, Jr. et al. | 310/323 X |
| 3,067,345 | 12/1962 | Harris | 310/323 |
| 3,336,529 | 8/1967 | Tygart | 310/323 X |
| 3,394,275 | 7/1968 | Lippmann | 310/323 X |
| 3,526,873 | 9/1970 | Burt | 340/683 X |
| 3,614,760 | 10/1971 | Zimmet et al. | 340/539 |
| 3,622,933 | 11/1971 | Van Den Broek | 310/323 X |
| 3,677,072 | 7/1972 | Weichbrodt et al. | 340/683 X |
| 3,786,413 | 1/1974 | Ross et al. | 340/58 |
| 3,798,626 | 3/1974 | Weichbrodt et al. | 340/669 |

Primary Examiner—John W. Caldwell, Sr.
Assistant Examiner—Joseph E. Nowicki
Attorney, Agent, or Firm—Donald R. Campbell; Marvin Snyder; James C. Davis

[57] ABSTRACT

A self-powered monitor unit with a tuned mechanical resonator power unit and a radio transmitter is mounted on every piece of rotating equipment being monitored, such as machinery with ball bearings. Bearing vibrations are sensed and the generation of a defect signal triggers the transmission of a radio signal modulated to identify the source. A central station receives and demodulates an emitted radio signal and displays the location with a fault condition. Large numbers of equipment can be monitored conveniently by unattended units.

5 Claims, 3 Drawing Figures

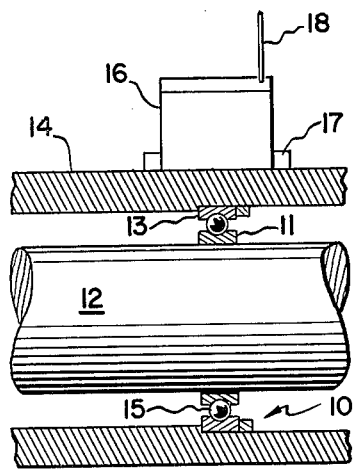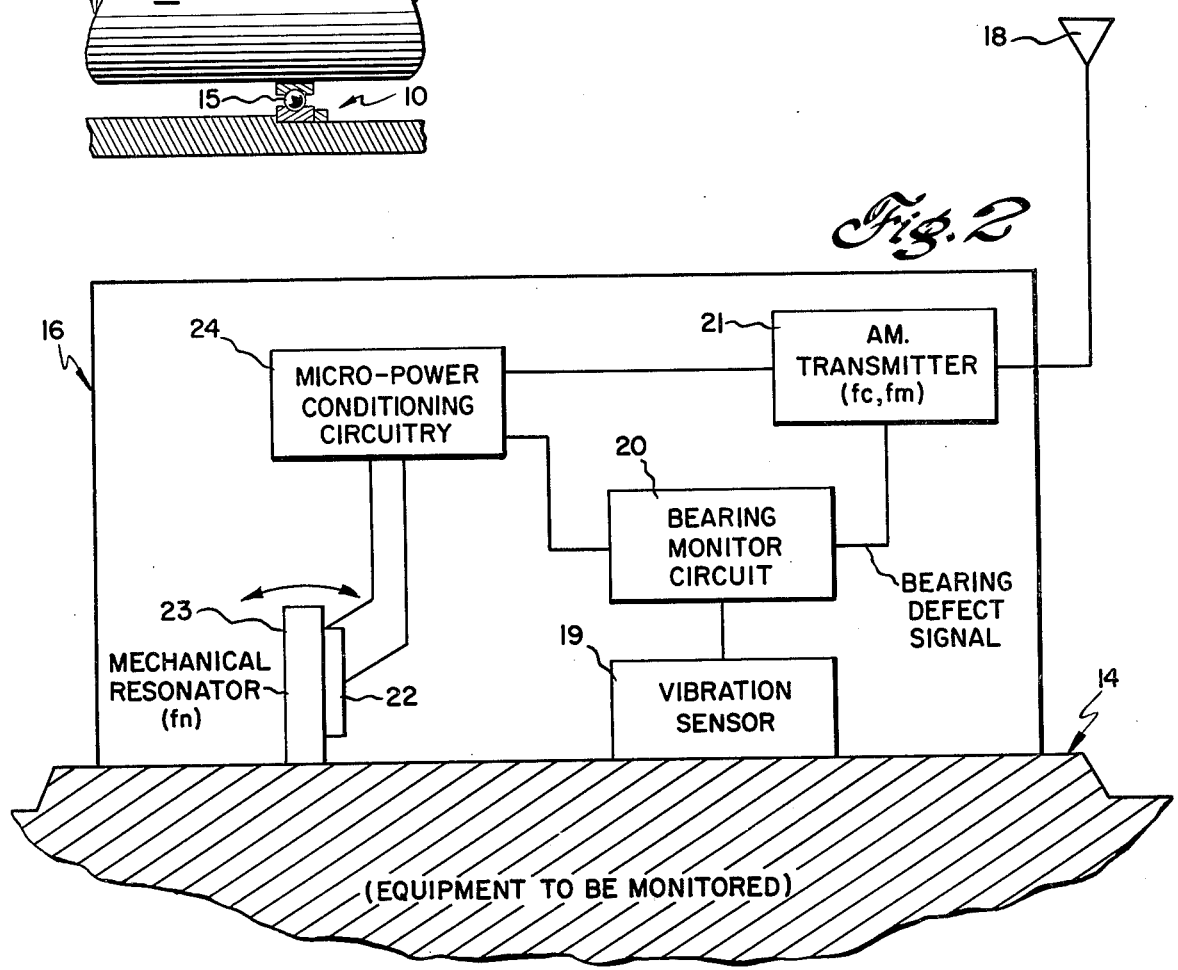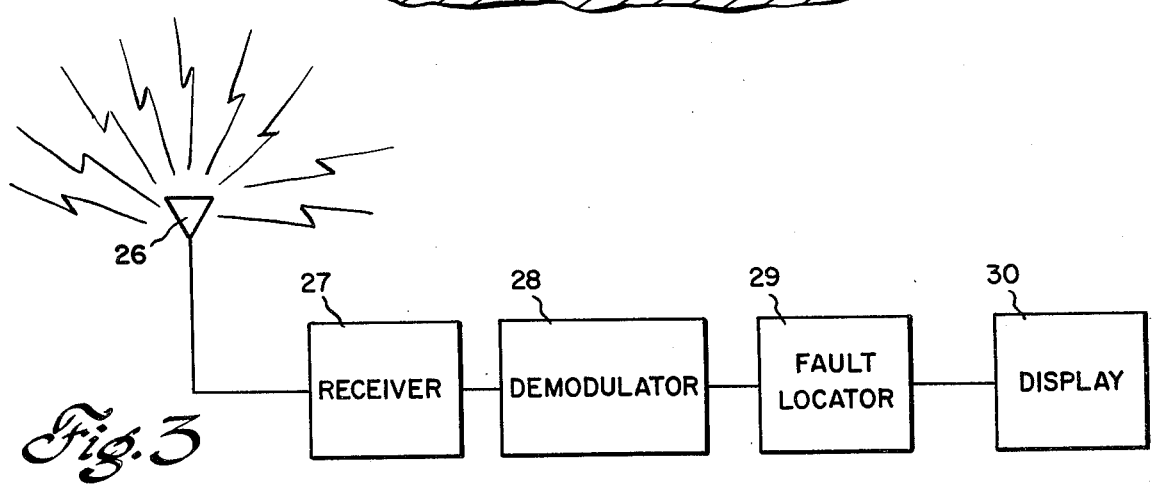

4,237,454

SYSTEM FOR MONITORING BEARINGS AND OTHER ROTATING EQUIPMENT

BACKGROUND OF THE INVENTION

This invention relates to a system for monitoring rotating equipment from a central station for the early detection of faults utilizing a self-contained and self-powered monitor located on each piece of equipment.

The need for techniques to monitor the performance of roller element bearings and detect their incipient failure has long been recognized. Several devices are known which measure the vibration emanating from a bearing and extract from the signal discriminants indicative of pending failure. One such device is the crest factor bearing monitor in U.S. Pat. No. 3,677,072 to B. Weichbrodt and B. Darrel granted on July 18, 1972. The sensitivity of this unit has been demonstrated in several successful applications, but the relatively high cost of building the device with meter relay and alarm limits its application to (a) dedicated installations on large, expensive, critical machines such as jet engines or (b) situations in which a large number of bearing installations can be periodically checked by service personnel with one or a few bearing monitors, such as production machinery in factories.

The advent of large scale integration (LSI) technology for manufacturing integrated circuits alters the situation drastically. The per unit cost of the crest factor bearing monitor is relatively low if volume production is assumed. Under this circumstance, dedicated installations can be justified in places where only periodic inspection could be considered in the past.

There remain certain implementation problems which must be addressed, however. Consider a large existing facility having a thousand or more bearing installations, specific examples of which are large power generating stations and chemical processing plants. It is feasible to provide an integrated circuit bearing monitor for each bearing. The monitoring system problems are principally supplying power to each bearing monitor and causing the output of the device to alert plant personnel to the bearing malfunction. Relative to the first, consider that in many applications, such as large motors and pumps, the only power available nearby is the high voltage/high amperage supply bus, and to tap off this is not a realistic solution. To signal a bearing defect to operating personnel, obvious possibilities are to activate an audible or visible indication of the bearing location or, via hardware, activate an alarm indicator in the plant's central control room. The problem with the former is that machines containing bearings may be unattended for long periods, and with the latter that this makes installation too expensive especially in a plant covering many acres.

SUMMARY OF THE INVENTION

A fault monitoring system effective in installations with many pieces of rotating equipment, such as pumps, machines with ball bearings, etc., employs a self-powered monitor unit on every piece of equipment which individually has the ability to signal a local fault condition to a central control point. Electrical power in each unit is derived from a tuned mechanical resonator operating at the rotational frequency of the equipment which is driven by the fundamental unbalance component of machine vibration. When the defect detection and transmitter circuitry are integrated circuits, sufficient power is generated. An amplitude-modulated (AM) radio transmitter in the unit is triggered by a defect signal produced by vibration signal processing circuitry and transmits to the central station a short duration radio signal that is modulated to uniquely identify the equipment with the fault condition. At the central station is a receiver for all monitor units and apparatus for determining the location or identity of the malfunctioning equipment.

The illustrative embodiment is a bearing monitoring system and each monitor unit is mounted on the equipment by permanent magnets to sense structure-borne vibrations emanating from the bearing. The mechanical resonator is comprised of a cantilever beam to which is attached a piezoelectric element, and there is a power conditioner. The AM transmitter in individual units has the same carrier frequency but a modulating frequency that is different from unit to unit and identifies every unit or piece of equipment. At the central station the radio signal is demodulated and the location of the fault condition is displayed. No signal or power wiring is needed for these monitors and they can be unattended except for occasional checks.

BRIEF DESCRIPTION OF THE DRAWING

FIG. 1 is a sketch of an individual monitor mounted on stationary machine structure to sense the vibrations of a roller element bearing;

FIG. 2 is a diagram of the components of a self-contained, self-powered bearing monitor; and FIG. 3 is a block diagram of radio receiving and fault location equipment at the central station.

DESCRIPTION OF THE PREFERRED EMBODIMENT

The present system makes bearing monitoring economically feasible for a number of very large industrial installations containing many pieces of rotating equipment having ball bearings. Power plants, large remote pumping stations and large petro-chemical complexes are examples. The latter may cover many acres and have thousands of pumps and compressors or other machinery with ball bearings to be checked, and this machinery may be unattended by operators or inspectors for long periods. The self-powered individual bearing monitor unit for each piece of equipment is made in a package about the size of a pack of cigarettes with a strong permanent magnet for mounting. A local bearing fault condition is communicated to the central station by a radio signal that is modulated or encoded to reveal the source of the malfunction.

In FIG. 1 is shown a part of a bearing 10 including an inner race 11 fastened to shaft 12, an outer race 13 fastened to the housing 14 or other stationary support structure, and a ball 15 between the inner and outer races. After a period of time, initial surface defects are developed in the bearing surfaces, and the bearing enters into a phase characterized by considerably higher wear until it finally fails to perform its function. To predict incipient bearing failure, it is necessary to detect the first surface defects while they are few and local, and this is realized by making use of the fact that an impact is generated everytime a defect in an otherwise smooth surface comes into rolling contact with any other smooth surface. The crest factor bearing monitor described in U.S. Pat. No. 3,677,072 to B. Weichbrodt and B. Darrel, the disclosure of which is incorporated herein by reference, measures the peak value of the vibration signal obtained from the machine elements and compares it with the mean value of the rectified vibration signal to obtain a ratio which is an indication of damage to the bearing and the extent of the damage. An alarm is actuated when the ratio signal rises to a designated level.

Self-contained bearing monitor unit 16 with attached permanent magnet 17 is mounted on stationary housing 14 at a position to sense structure-borne vibrations emanating from bearing 10, and has an AM transmitter and antenna 18 for sending a radio signal to the central station only upon detection of a damaged bearing. Referring to the schematic of bearing monitor 16 in FIG. 2, an accelerometer or other vibration sensor 19 generates an electrical signal corresponding to the sensed bearing vibrations which is fed to a bearing monitor circuit 20. The circuitry of the crest factor bearing monitor in the foregoing patent is reduced to a single integrated circuit chip, and this not only substantially reduces the cost but also slashes the circuit's power requirements. When the output of bearing monitor circuit 20 reaches a prescribed level for a predetermined interval, a bearing defect signal is generated and triggers a high frequency AM (amplitude-modulated) transmitter 21 which emits a carrier frequency ($f_c$) modulated by a fixed, identifying frequency ($f_m$) for approximately one second. The carrier frequency is the same for all bearing monitor units within a system installation but every individual unit is set to emit its own modulating frequency. Power to drive both the defect detection and transmitting circuitry is derived from a piezo-crystal or piezo-ceramic element 22 which is attached to a cantilever beam 23 and is a tuned mechanical resonator operating at the rotational frequency ($f_m$) of the rotating equipment on which the bearing monitor unit is mounted. Cantilever beam 23 is secured at its lower end to the case of the monitor unit and is free at its upper end to vibrate as shown by the double ended arrow upon being excited by vibrations of the frequency for which it is tuned. The beam may also be referred to as a vibrating reed. Thus, the ever present fundamental unbalance component of machine vibration drives the resonant power unit.

A piezoelectric-crystal element is a high impedance power supply which generates high voltage, low current electrical power. Only a few milliwatts of power are generated but this is sufficient to run the detection circuitry continuously and, if power is stored, for occasional operation of the radio transmitter. Micro-power conditioning circuitry 24 of conventional design is needed to step down the voltage and step up the current to levels suitable for the bearing monitor and radio transmitter integrated circuits. Power for transmitter operation is stored in a capacitor which is discharged in response to the bearing defect signal trigger. The radio signal has enough power to be received several hundred yards away. The minimum requirements, for instance, are a one-half second pulse at a 20 milliwatt power level. Virtually all electrically driven rotational equipment operates either at 1800 rpm or 3600 rpm, which corresponds to 30 hertz and 60 hertz. Therefore, only a few different mechanical resonators may be required, and this may also be convenient from the standpoint of the power conditioning task.

One central receiver in the control room or central station monitors the known carrier frequency, $f_c$, on which the bearing monitors operate. Upon detecting the signal, the receiver circuitry determines the modulating frequency, $f_m$, and triggers a control room alarm and display indicating which bearing monitor location is the source. The central room equipment illustrated in FIG. 3 includes a receiving antenna 26 and a single receiver 27 tuned to the carrier frequency. A demodulator 28 determines the modulating frequency of the received signal and presents this information to a fault locator 29, which can be a microprocessor with a look-up table giving the piece of equipment with the fault condition or the number of the monitor unit at that location. An audible alarm is actuated and in addition there is a visual display device giving the output information which pinpoints the malfunctioning equipment.

Installation of bearing monitor unit 16 is relatively simple and requires nothing more than placing the units over bearings and logging the unit identifying numbers versus location. No power or signal wiring is required for the bearing monitor units, and periodic maintenance can be minimal and operational checks can be carried out by applying a synthesized vibration signal simulating a damaged bearing to the unit and verifying the rf emission. All receiver and alarm circuitry requiring power resides in a signal unit within the central station. Thus, the installation and maintenance costs are minimized, amounting to little more than the cost of the hardware itself.

There are many different ways for modulating or encoding the carrier frequency, and the radio transmitting mode is selected on the basis of a minimum power requirement to transmit over the known distance. Specific radio transmission and reception circuits are detailed out in The Radio Amateur's Handbook, 1972, and in many other references.

The individual monitor units and the monitoring system have utility in the monitoring of other parts of rotating equipment such as for the detection of defects in gear trains and gear assemblies. The latter is further explained in U.S. Pat. No. 3,677,072. Another application is the continuous checking for malfunctions of journal bearings and other metal surfaces in contact with one another. Still another is the foreign object impact detector for multibladed fluid engines such as gas turbines or the compressors of jet engines. The equipment is monitored for the presence of foreign and internally originated free objects which could cause damage to the blades and other components if the equipment is allowed to continue operation. Reference may be made to U.S. Pat. No. 3,798,626 to B. Weichbrodt and B. Darrel. Both of the foregoing patents are assigned to the assignee of this invention.

While the invention has been particularly shown and described with reference to several preferred embodiments thereof, it will be understood by those skilled in the art that various changes in form and details may be made therein without departing from the spirit and scope of the invention.

The invention claimed is:

1. A system for monitoring rotating machinery at many locations and communicating a fault condition to a central station, said machinery inherently having a fundamental unbalance component of machine vibration, comprising:

a self-powered monitor unit removably mounted on every piece of machinery on a stationary structure thereof at a position to sense structure-borne vibrations;

each monitor unit including a tuned mechanical resonator for generating electrical power which operates at the rotational frequency of the machinery and is driven by the fundamental unbalance component of machine vibration; a power conditioner for converting the generated electrical power; a vibration sensor for sensing said structure-borne vibrations and continuously producing an electrical vibration signal; signal processing circuitry for continuously processing said vibration signal and producing a defect signal upon the occurrence of a fault condition; and radio transmitter circuitry triggered by said defect signal for transmitting to the central station a radio signal that uniquely identifies the piece of machinery with a fault condition;

said tuned mechanical resonator comprising a cantilever beam and an attached piezoelectric element; said power conditioner being connected to said piezoelectric element and supplying electrical power to said signal processing circuitry continuously so long as said machinery is rotating and to said radio transmitter circuitry only upon triggering by said defect signal.

2. The system of claim 1 wherein the radio transmitter circuitry of all monitor units has the same carrier frequency but a different modulating frequency that identifies every piece of rotating equipment; and wherein the system further includes a radio receiver, a demodulator, and a fault locator apparatus at the central station for receiving and demodulating the radio signals from all monitor units and displaying an identification of the faulty machinery.

3. The system of claim 1 wherein each monitor unit has a permanent magnet for removable mounting on the piece of machinery.

4. A system for monitoring roller element bearings in rotating machinery at many locations for fault conditions comprising:

a self-powered monitor unit removably mounted on every piece of machinery on a stationary structure thereof at a position to sense structure-borne vibrations emanating from the bearing;

each monitor unit including a tuned mechanical resonator for generating electrical power which operates at the rotational frequency of the machinery and is driven by the fundamental unbalance component of machine vibration; a power conditioner for converting the generated electrical power; a vibration sensor for sensing the bearing vibrations and generating an electrical vibration signal; a bearing monitor circuit for continuously processing said vibration signal and producing a defect signal upon the occurrence of a fault condition; radio transmitter circuitry triggered by said defect signal for transmitting to the central station a radio signal that uniquely identifies the piece of machinery with a fault condition;

said power conditioner being connected to said mechanical resonator and supplying electrical power to said bearing monitor circuit continuously so long as said machinery is rotating and to said radio transmitter circuitry only upon triggering by said defect signal; and a receiver and fault locator apparatus at a central station for receiving the radio signals and displaying an identification of the faulty machinery.

5. The system of claim 4 wherein said tuned mechanical resonator is comprised of a cantilever beam and an attached piezoelectric element.

* * * * *